(12) United States Patent
Velez-Bernal et al.

(10) Patent No.: US 9,801,895 B1
(45) Date of Patent: Oct. 31, 2017

(54) CREAM FORMULATION WITH AMPHOTERICIN B AND OIL IN WATER USEFUL FOR TOPICAL APPLICATION TO MUCOUS TISSUE AND SKIN AGAINST DISEASES PRODUCED BY LEISHMANIASIS

(71) Applicants: UNIVERSIDAD DE ANTIOQUIA, Medellin, Antioquia (CO); HUMAX PHARMACEUTICAL S.A., Itagui, Antioquia (CO)

(72) Inventors: Ivan Dario Velez-Bernal, Medellin (CO); Sara Maria Robledo-Restrepo, Medellin (CO); Martha Beatriz Robledo-Restrepo, Medellin (CO); Alba Lucia Ceballos-Maya, Medellin (CO); Newar Andres Giraldo-Alzate, Medellin (CO); Alvaro Gomez-Zuluaga, Medellin (CO); Juan Jose Zuluaga-Rivera, Medellin (CO)

(73) Assignees: HUMAX PHARMACEUTICAL S.A. (CO); UNIVERSIDAD DE ANTIOQUIA (CO)

( * ) Notice: Subject to any disclaimer, the term of this patent is extended or adjusted under 35 U.S.C. 154(b) by 0 days.

(21) Appl. No.: 13/952,351

(22) Filed: Jul. 26, 2013

(51) Int. Cl.
 *A61K 31/7048* (2006.01)
 *A61K 9/06* (2006.01)

(52) U.S. Cl.
 CPC .......... *A61K 31/7048* (2013.01); *A61K 9/06* (2013.01)

(58) Field of Classification Search
 CPC .............................. A61K 31/7048; A61K 9/06
 See application file for complete search history.

(56) References Cited

U.S. PATENT DOCUMENTS

| | | | |
|---|---|---|---|
| 5,444,052 A * | 8/1995 | Pieringer et al. | 514/31 |
| 5,736,553 A * | 4/1998 | Wick et al. | 514/293 |
| 6,492,395 B1 * | 12/2002 | Scheiwe et al. | 514/327 |
| 6,846,837 B2 * | 1/2005 | Maibach et al. | 514/350 |
| 2006/0204526 A1 * | 9/2006 | Lathrop | A61K 9/0014 424/400 |
| 2009/0258000 A1 * | 10/2009 | O'Donnell, Jr. | A61K 31/7048 424/94.61 |
| 2010/0196293 A1 * | 8/2010 | Dal Farra et al. | 424/59 |

OTHER PUBLICATIONS

Layegh et al, "Efficacy of Topical Liposomal Amphotericin B versus Intralesional Meglumine antimoniate (Glucantime) in the Treatment of Cutaneous Leishmaniasis", Journal of Parasitology Research, 2011.*
Vardy et al, "Topical Amphotericin B for Cutaneous Leismaniasis", Arch. Dermatol. vol. 135, pp. 856-857, Jul. 1999.*
Gattefosse website, http://www.gattefosse.com/en/products/emulium-delta.html, accessed online on Aug. 30, 2013.*
Chang et al., AAPS J., 2013, 15(1), p. 41-52, published online Oct. 9, 2012.*
Moreno et al., Pharm. Res., 2001, 18(3), p. 344-351.*

* cited by examiner

*Primary Examiner* — Jonathan S Lau
(74) *Attorney, Agent, or Firm* — Hoglund & Pamias, PSC; Robert J Rios

(57) ABSTRACT

The cream formulation of the present invention is a topical cream made with antimycotic (amphotericin B) and a mixture of excipients where the water present in the formulation smoothes inflamed tissue. The cream has a particular application for the treatment of cutaneous leishmaniasis and mucosal leishmaniasis in humans and animals. The topical application avoids the risks of toxicity and the gastrointestinal hassles of pills treatments. It has greater acceptability from patient and does not require of valuations before, during or after treatment to check toxicity levels of the liver, kidney and heart.

8 Claims, 3 Drawing Sheets

Amphotericin B.

| COMPONENTS | FUNCTION | Quantity (g) *100g |
|---|---|---|
| Amphotericin B | Therapeutic Agent | 3.00 |
| Water | Vehicle | 73.32 |
| Sodium methylparaben | Preservative | 0.10 |
| sodium propylparaben | Preservative | 0.02 |
| Monobasic sodium phosphate | pH modifying agent | 0.96 |
| Cetyl alcohol | Emollient, oily phase | 5.00 |
| Light mineral oil | Emollient, oleaginous vehicle | 4.00 |
| Emulium Delta | Emulsifier, amphoteric surfactant | 2.90 |
| White petrolatum | Oily phase, hardening agent | 10.00 |
| Glycerol monostearate | Non-ionic emollient, emulsifier | 0.70 |

FIG. 2

|           | Therapeutic efficacy (%) | | |
|-----------|------|----------------------|---------|
| Group (n) | Cure | Clinical improvement | Failure |
| A (8)     | 62,5 (n=5) | 12,5 (n=1) | 25 (n=2) |
| B (8)     | 75 (n=7)   | 25,0 (n=1) | 0 (n=0)  |
| C (8)     | 12,5 (n=1) | 12,5 (n=1) | 75 (n=6) |
| D (8)     | 25 (n=2)   | 25 (n=2)   | 50 (n=4) |
| E (7)     | 71,4 (n=5) | 14,3 (n=1) | 14,3 (n=1) |
| F (8)     | 0 (n=0)    | 37,5 (n=3) | 50 (n=5) |

FIG. 3

CREAM FORMULATION WITH AMPHOTERICIN B AND OIL IN WATER USEFUL FOR TOPICAL APPLICATION TO MUCOUS TISSUE AND SKIN AGAINST DISEASES PRODUCED BY LEISHMANIASIS

BACKGROUND OF THE INVENTION

There are three main clinical manifestations of leishmaniasis, which are currently classified as visceral, mucocutaneous, and cutaneous leishmaniasis. The clinical form of leishmaniasis is determined by the *Leishmania* species, geographical location, and immune response of the host. The leishmaniasis diseases are endemic in 98 countries, frequently with one type being more of a threat over the other two in specific regions. It is estimated that more than 350 million people are at risk, 12 million people are affected worldwide, with 2 million new cases reported per year (1.5 million CL and 0.5 million VL). VL causes 50.000 to 60.000 deaths annually. The leishmaniasis are widely dispersed, with transmission to humans on five continents, but the human disease burden is concentrated mainly in a few major foci. On the other hands Chagas disease, also known as American trypanosomiasis, is a potentially life-threatening illness caused by the protozoan parasite, *Trypanosoma cruzi* (*T. cruzi*). It is found mainly in Latin America, where it is mostly transmitted to humans by the faeces of triatomine bugs. An estimated 10 million people are infected worldwide, mostly in Latin America where Chagas disease is endemic. More than 25 million people are at risk of the disease. It is estimated that in 2008 Chagas disease killed more than 10,000 people.

The classification system divides the genus *Leishmania* into two sub-genera: *Leishmania* (*L*) *sensu-stricto*, present in both Old and New World, and *Viannia* (*V*), restricted to the New World. Within these two sub-genera, various species complexes have been individualized (Rioux, 1990). Currently, at least twenty different species are recognized as human infectants. The most prevalent species involved in human cases of leishmaniasis are *L.* (*L*) *donovani, L.* (*L*) *infantum, L.* (*L*) *mexicana, L.* (*L*) *amazonensis, L.* (*L*) *tropica, L.* (*L*) *major, L.* (*L*) *aethiopica, L.* (*V*) *braziliensis, L.* (*V*) *guyanensis, L.* (*V*) *panamensis* and *L.* (*V*) *peruviana*. Each of these species is found in different locations worldwide and is responsible for causing different types of leishmaniasis (Center for Disease Control, 2002).

Visceral leishmaniasis is the most pathogenic of the three types. It is caused by species of *L.* (*L*) *donovani* complex and *L.* (*L*) *infantum*. The common symptoms include irregular fever, weight loss, swelling of the spleen and liver and anemia (World Health Organization, 2010). If left untreated, visceral leishmaniasis will lead to death. Endemic *L.* (*L*) *infantum* visceral leishmaniasis affects mainly children and *L.* (*L*) *donovani* VL affects people of any age group living in urban and rural areas. The onset of this type is usually abrupt, but symptoms may appear 3 weeks to 2 years after exposure.

The clinical features of cutaneous leishmaniasis (CL) tend to vary between and within regions, reflecting different species of parasite or the type of zoonotic cycle concerned, immunological status and also genetically determined response of patients. Two weeks to 2 months after the insect byte, the lesion starts as a papule or nodule at the site of inoculation; its grows slowly, a crust develops centrally, which may fall away, exposing an ulcer with a raised edge and variable surrounding induration which heals gradually over months or years, leaving a depressed scar with altered pigmentation. Satellite nodules at the edge of the lesion are common. Cutaneous leishmaniasis has a wide variety of clinical presentations. WHO estimated in 1500000 the number of new cases yearly in the world. In the Old World CL is caused by 5 species: *L infantum, L major, L tropica, L aethiopica* and *L donovani*. In the Americas CL are caused by multiple species of both the *Leishmania* and *Viannia* subgenera. The clinical forms included localized, disseminated, diffuse and atypical CL and mucocutaneous leishmaniasis (MCL).

Mucocutaneous leishmaniasis is caused by the metastasis from the skin to the naso-oro pharyngeal mucosal tissues by lymphatic or hematogenous dissemination of *L braziliensis, L panamensis* and *L guyanensis*.

Access to medicines for the treatment of VL, CL and MCL is problematic in the poverty-stricken countries that have the highest burden of cases (WHO 2010). Most research to treat leishmaniasis is focused on the development of improved chemotherapies because current drugs are unsatisfactory (Croft and Yardley, 2002). Pentavalent antimonials, such as meglumine antimoniate and sodium stibogluconate are the most used anti-leishmanial drugs. They are chemically similar and their toxicity and efficacy are related to their antimonial content. While they can be therapeutic, they have unsatisfactory side effects such as nausea, vomiting, anorexia, abdominal pain, myalgia, arthralgia, headache, metallic taste and lethargy. Systemic toxicity (cardiac, renal and hepatic), chemical pancreatitis, decreases in RBCs (Red Blood Cell Count), WBCs (White Blood Cell Count) and platelet counts and reversible peripheral neuropathy (Berman, 1997).

Additionally, these drugs require prolonged treatment (Shyam and Madhukar, 2002; Berman, 2003). The treatment with antimonials includes repeated [daily intramuscular or intravenous] injections for 20-28 days, requiring medical supervision. It is recommended that 20 mg/kg body weight be injected daily over that period of time (Berman, 1997). In addition to these drawbacks, *Leishmania* parasites are also becoming increasingly resistant to these treatments (Shyam and Madhukar, 2002; Berman, 2003).

Amphotericin B deoxycholate or lipid formulations of amphotericin B is a secondary treatment used for leishmaniasis, especially when antimonial treatment has not been effective (Markle and Makhoul, 2004). This treatment is parenteral in nature and also highly toxic. It was found, however, that a total dose of 15 mg/kg body weight is 100% effective and a dose of 10 mg/kg of liposomal amphotericin B is 97% effective against the Indian visceral disease (Berman, 2003 Sundar 2011). A liposomal formulation reduces the toxicity (Sundar S, 2010), but at a higher cost.

Other currently used drugs include the alkyl-glycerophosphocholine (miltefosine), Paromomycin, pentamidine isethionate, and ketoconazole. Miltefosine was originally developed as an oral anticancer drug but was shown to have antileishmanial activity. At a dose of 2.5 mg/kg per day for days is recommended by WHO as systemic treatment for Visceral leishmaniasis, post kala-azar dermal leishmaniasis and for New world cutaneous leishmaniasis caused by *L mexicana, L panamensis* and *L guyanensis* and for mucocutaneous leishmaniasis in Bolivia. Miltefosine commonly induces gastrointestinal side-effects such as anorexia, nausea, vomiting (38%) and diarrhea (20%). Most episodes are brief and resolve as treatment is continued. Occasionally, the side-effects can be severe and require interruption of treatment. Skin allergy, elevated hepatic transaminase concentrations and, rarely, renal insufficiency may be observed. Miltefosine should be taken after meals, and, if multiple doses are to be taken, they should be divided. Miltefosine is potentially teratogenic and should not be used by pregnant women or women with child-bearing potential for whom adequate contraception cannot be assured for the duration of treatment and for 3 months afterwards (WHO 2010) Paromomycin (aminosidine), an aminoglycoside antibiotic, usually administered intramuscularly, are under study. The 15 mg/kg sulfate is equivalent to 11 mg/kg of base, and the 20 mg/kg sulfate is equivalent to 15 mg/kg of base. Mild pain at the injection site is the commonest adverse event (55%). Reversible ototoxicity occurs in 2% of patients. Renal toxicity is rare. Some patients may develop hepatotoxicity, indicated by raised hepatic enzyme concentrations; tetany has also been reported. (WHO 2010) Paromomycin ointments plus gentamicine or plus methyl benzethonium chloride twice daily for 20 days as shown encouraging results for the treatment of CL. Pentamidine isethionate given intramuscular or by intravenous infusion of 4 mg salt/Kg per day every other day for 3 doses, is recommended for the systemic treatment of CL causes by *L panamensis* and *L guyanensis* severe adverse events as diabetes mellitus, severe hypoglycaemia, shock, myocarditis and renal toxicity are recorded. Ketokonazole have variable efficacy in leishmaniasis treatment and is recommended by WHO for *L mexicana* cutaneous leishmaniasis at a daily adult oral dose of 600 mg for 28 days.

Thermotherapy applications for 30 seconds showed encouraging results as an alternative treatment of CL. The therapy consists in one or two applications of localized heat (50° C.). This therapy has shown as effective as intralesional Sb5+(70% cure rate) in Afghanistan (*L. tropica*) and more effective (70% cure rate) than systemic Sb5+ in *L. major* cutaneous leishmaniasis. This device is expensive, and the initial evolution of the disease after thermotherapy is complicated by second-degree burns. Local anaesthesia is necessary.

Cryotheraphie with liquid nitrogen (−195° C.) applied to the lesion once or twice weekly up to 6 weeks also showed encouraging results as an alternative treatment of CL. Liquid nitrogen application requires specific (usually expensive) devices and a skilled health-care provider. Cryotherapy is widely available at dermatology departments but generally not in the field, and the supply chain for liquid nitrogen requires heavy equipment.

Quaternary ammonium compounds such as octadecyltrimethyl ammonium bromide and dodecyltrimethyl ammonium bromide have also been reported to inhibit the growth of *L. major* promastigotes (Zufferey and Mamoun, 2002). The use of alkyl quaternary ammonium compounds including certain choline analogs for treating or preventing fungal and trypanosomal (e.g., Leishmaniasis) infections is described by Mamoun (2006). The compounds seem to inhibit or perturb choline transport into the parasites, thus inhibiting parasites growth. Common side-effects are anorexia, vomiting, nausea, abdominal pain, malaise, myalgia, arthralgia, headache, metallic taste and lethargy. Electrocardiographic changes depend on the dose and duration of treatment, the commonest being T-wave inversion, a prolonged Q-T interval and arrhythmia. Cardiotoxicity and sudden death are serious but uncommon side-effects. Prolongation of a corrected Q-T interval (>0.5 sec) signals the likely onset of serious and fatal cardiac arrhythmia. Pancreatic enzyme concentrations are commonly raised, but clinical pancreatitis is uncommon. Elevated liver enzyme concentrations, leukopenia, anaemia and thrombopenia are not uncommon.

Other quaternary ammonium salts that are known antibacterials, such as methylbenzethonium chloride, benzethonium chloride, cetalkonium chloride, benzalkonium chloride, and cetrimonium bromide have been used in combination with other drugs such as paromomycin and meglumine antimoniate (Soto et al., 1998; Krause and Kroeger, 1994; Carter et al., 1989; El-On et al., 1985, 1984); as a well as benzethonium chloride, in combination with other drugs such as hexadecyl-phosphorylcholine (Iqbal et al., 2006).

Chagas disease can be treated with either benznidazole or nifurtimox. Both medicines are almost 100% effective in curing the disease if given soon after infection at the onset of the acute phase. However, the efficacy of both diminishes the longer a person has been infected. Benznidazole and nifurtimox should not be taken by pregnant women or by people with kidney or liver failure. Nifurtimox is also contraindicated for people with a background of neurological or psychiatric disorders (World Health Organization, 2010).

Multiple metabolic pathways and specific molecular targets have been studied in trypanosomatid parasites. Membrane lipid biosynthesis pathways are a viable target for anti-trypanosomal compounds since phospholipids have an important role in the cell biology of the parasite and membrane lipid composition differs significantly when compared to mammals.

SUMMARY OF THE INVENTION

The present invention belongs to the field of pharmaceutical chemistry with application in the human and animal medicine. The invention provides a topical cream made with antimycotic (amphotericin B) and a mixture of excipients where the water present in the formulation smooths inflamed tissue. The evaporation of water increases the concentration of the drug in the cream product formulation, creating an adherent film that releases the drug. This evaporation does not form a totally occlusive film, the cream product formulation can deposit lipids and others wetting on the surface and within stratum corneum, restoring the hydration capacity of the skin, acting as a vehicle, for the treatment of infectious diseases of skin and mucous, especially those caused by parasites, fungi and bacteria and particular application for the treatment of cutaneous leishmaniasis and mucosal leishmaniasis in humans and animals.

According to an aspect of the invention, the cream formulation has amphotericin B as an active ingredient.

According to another aspect of the invention, the formulation has a pharmaceutical antifungal active ingredient from 0.3% to 3.0% by weight.

According to still another aspect of the invention, the other components of the cream formulation are excipients.

According to one aspect of the invention, the cream formulation improves the prior art because it allows the active ingredient to be effective in the deep layers of the skin, providing a better external appearance during the cicatrization process and a better cosmetic appearance of the skin.

According to another aspect of the invention, topical application of the cream formulation avoids the risks of toxicity and the gastrointestinal hassles of pills treatments.

According to yet another aspect of the invention, the cream formulation is less expensive and has a wide accessibility, being between 15 times and 20 times less expensive than current treatments.

According to still another aspect of the invention, the cream formulation has greater acceptability from patient and does not require of valuations before, during or after treatment to check toxicity levels of the liver, kidney and heart.

According to another aspect of the invention, the excipients allow fixating the antifungal to the skin for an amount of time sufficient to achieve the desired healing effect.

BRIEF DESCRIPTION OF THE DRAWINGS

Further features and advantages of the invention will become apparent from the following detailed description taken in conjunction with the accompanying figures showing illustrative embodiments of the invention, in which:

FIG. 2 shows a table indicating the final formulation for Amphotericin B (3%) cream with components, function and quantity, according to an embodiment of the invention.

FIG. 3 shows the therapeutic efficacy of the cream formulation, according to an embodiment of the invention.

Figure 1:
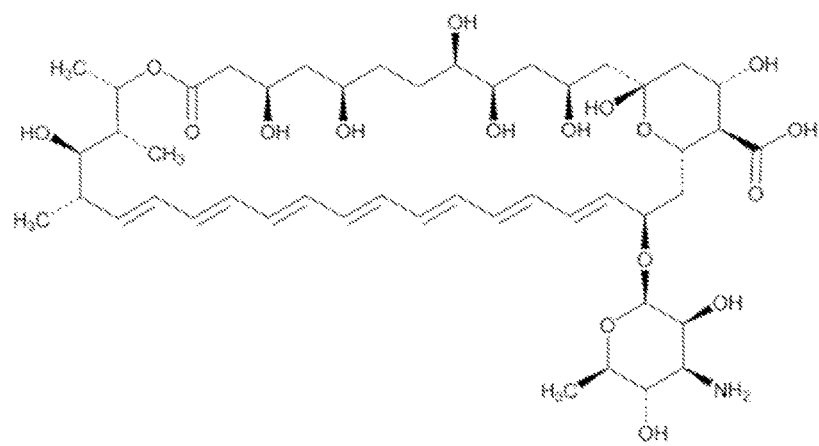
FIG. 1 illustrates the chemical structure of Amphotericin B, according to an embodiment of the invention.

Throughout the figures, the same reference numbers and characters, unless otherwise stated, are used to denote like elements, components, portions or features of the illustrated embodiments. The subject invention will be described in detail in conjunction with the accompanying figures, in view of the illustrative embodiments.

DETAILED DESCRIPTION OF THE INVENTION

The cream product formulation oil in water useful is amphotericin B with a mixture that has a pharmaceutical active ingredient from 0.3% until 3.0% in antifungal weight (Amphotericin B, the other part in weight, are the excipients in the formula). This mixture with Amphotericin B (3%) ensures the organoleptic properties (consistency, viscosity, among others) of the cream, and the appropriate absorption of to the product. This cream is useful for topical application in mucous and skin against diseases produced by parasites, fungus and bacteria.

The main characteristics of the cream is its homogeneity, smoothness, free particle and easy to use. The cream is insoluble in water, in anhydrous alcohol, ether, benzene and toluene; soluble in dimethylformamide, dimethylsulfoxide and propylene glycol; slightly soluble in metanol.

On the other hand, the excipients used are Sodium methylparaben, Monobasic sodium phosphate, Light mineral oil, White petrolatum, Carboximetilcellulose, BHA, Monoestearate de glyceril and polietilenglycol 100, DMEG, Carbopol 940, Trietilamine, Alcohol cetoestearilic, Arlacel 165. The excipients that constitute the formula confer the cream an excellent appearance, emolliency, stickiness, viscosity, among other physical properties required for this type of pharmaceutical form.

In Vivo Therapeutic Response of Cream Product Formulation on *L. amazonensis*

The evaluation of the therapeutic response and toxicity of the cream formulation was carried out in the hamster model for cutaneous leishmaniasis (Robledo et al, 2012) using the Golden hamsters (*Mesocricetus aerates*). Animals were handled under the same micro and macro environmental conditions. Experimental groups were named accordingly: A. Cream product formulation once a day; B. Cream product formulation twice a day; C. Placebo once a day and D. Placebo twice a day. Additionally, two groups of animals were used as control groups. One of them (E) was used to evaluate meglumine antimoniate as a control medicine at the curative (120 mg/kg day×10 days) and the other group (F) were infected and untreated animals.

The effectiveness of each treatment was assessed comparing the lesion sizes prior to and after treatments, using the following score system: cure (healing of 100% area and complete disappearance of the lesion); clinical improvement (reducing the size of the lesion in >30% of the area); clinical failure (reduction in the size of the lesion lower than 30% or increase in the size of the lesion); relapse (reactivation of lesion after cure).

The efficacy of treatment with topical formulation of 3% amphotericin B is summarized in FIG. 3. Overall, cream product formulation when applied once a day during 15 days did produce a 62.5% of cure. This percentage increased to 75% when applied twice a day during 15 days. The efficacy of meglumina antimoniate was 71%.

FIG. 3 shows: (A) cream product formulation applied once a day×15 days, (B) cream product formulation applied twice a day×15 days, (C) topical placebo applied once a day×15 days, (D) topical placebo applied twice a day×15 days, (E) intramuscular meglumine antimoniate applied once a day×10 days, (F) infected and untreated control. Therapeutic Efficacy in Hamsters Treated with 3% Amphotericin B Ointment vs Placebo and Meglumine Antimoniate. In Vivo Toxicity of Cream Product Formulation on *L. amazonensis*

Hamsters were weighed weekly from the beginning of the experiment until three months after the end of the treatment. No any detrimental effect was observed for any scheme on the body weight gain of the animals treated with the topical formulation. These results suggest that topical formulation of 3% amphotericin B ointment and placebo did not affect significantly the weight gain in the animals treated in comparison with meglumina antimoniate.

Effect of Treatments on Serum Levels of BUN, Creatinine and ALT:

There were no significant changes in pre-treatment and post-treatment serum level of ALT, BUN and creatinine analytes supporting no evidence of any effect on them in any treatment schedule, or assessment treatment.

Effect of Treatments in Histopathology Changes:

In the skin, changes observed in all animals, including those infected and untreated hamsters, were minerals, congestion, fibrosis and hyperplasia with necrosis. In general, the diagnosis was granulomatous dermatitis for untreated and treated animals. In some animals of all the different groups of treatments was also observed granulomatous dermatomyositis and cutaneous pyogranulome.

In the liver no lesions or significant changes associated with amphotericin B were present. There were also no changes associated with the treatment scheme, one or two applications per day. In the kidney, no significant changes were observed associated with amphotericin B.

In conclusion, topical treatment with 3% amphotericin B ointment showed an efficacy rate of 62.5% when used once a day during 15 days. The efficacy rate increased to 75% when was applied twice a day during the same 15 days. This efficacy was comparable to the efficacy showed by meglumina antimoniate (71%).

No toxic effects associated to the 3% amphotericin B ointment were observed when used once or twice a day during 15 days, evidenced by no any detrimental effect on the body weight gain of the animals, or absence of any significant changes in seric level of ALT, BUN and creatinine analytes or histology of liver, kidney and skin.

Safety/Tox Data (GLP Studies)

In Vivo Skin Absorption/Penetration. This Study Followed the OECD Test Guideline 427.

In this method the test substance is applied to the clipped skin of animals and is allowed to remain in contact with the skin for a fixed period of time under a non-occlusive cover to prevent ingestion of the test preparation. At the end of the exposure time the cover is removed and the skin is cleaned with an appropriate cleansing agent, the cover and the cleansing materials are retained for analysis and a fresh cover applied. Animals were exposed to the test preparation during 8 hours. One group was killed at the end of the exposure period. Other group was sacrificed at 48 hours and a third group was sacrificed at 72 hours after the end of exposure. The samples were assayed for concentration of amphotericin B by HPLC and the degree of percutaneous absorption was estimated.

Experimental animals: Females (nulliparous and non-pregnant) rats (Wistar), healthy, with intact skin were used from the spf (specimen pathogen free) animal facility of University Research Center at the University of Antioquia.

Dosage and treatment groups: 12 animals were used, divided into three groups, which were applied the product under study. Four animals for each time interval: 8 h, 48 h and 72 h.

Environmental conditions and housing: The animals were randomly distributed in individual cages. During the experiment, water management and food was ad libitum. Macro environment: Temperature between 19° C. and 22° C., relative humidity 50%-60%, from 16 to 20 air changes per hour, artificial lighting with white light/dark cycle of 12/12 hours, regulated by a timer. Also free of noise pollution and smell. Microenvironment: Rats were placed in the room devoted to this species in the experimental spf animal facility, housed individually in transparent boxes.

Test conditions: As test substance, it was used a preparation containing 3% of amphotericin B that is the final product that will be applied to patient.

After 8 hours of exposure to 3% amphotericin B ointment and after washing with PBS, amphotericin B levels were detected in samples from stratum corneum at 0.04 µg/mL and urine at 0.011 µg/mL. 24 and 48 hours later, amphotericin B was detected in samples from and feces at 3.48 µg/mL and 0.1 µg/mL, respectively. No amphotericin B was detected in serum at any time point.

The in vivo skin absorption/penetration study showed that after a single application of 40 mg of 3% amphotericin B ointment a high percentage of amphotericin B (99.842%) was absorbed while the retention was only 0.158%.

Renal elimination of amphotericin B has a faster clearance. Low concentrations in urine samples were found 8 hours after exposure, but it was not detected at 48 and 72 hours. On the other hands, the presence of amphotericin B in feces at 24 and 48 hours after exposure at concentrations of 3.48 µg/mL and 0.099 µg/mL could be due to the elimination half-life of amphotericin of 24 hours to 48 hours, as demonstrated previously.

In Vitro Skin Irritancy Tests: (Adapted from OECD Guideline No. 439)

For evaluation of skin irritation a test designed to predict acute skin irritation of chemicals by measuring its cytotoxic effect, was used using the MTT assay in reconstructed human epidermis model (RHE).

In histological sections of tissues exposed to 5% SDS (positive control) it was observed several layers of nucleated cell including layers of granular cells. A detached thick stratum corneum was also observed that is followed by an atrophic spinous stratum. The granular layer was not evidenced and the subepithelial dermis was not represented.

In Vitro Eye Irritation (Adapted from OECD Guideline No. 439):

For evaluation of eye irritation (cornea tissue) we used the Acute Eye irritation test using Reconstructed Human corneal Epithelium tissue (HCE).

Each test substance (cream product formulation, placebo, positive and negative controls) was applied topically. After 10 minutes, 2 hours and 24 hours of treatment cell viability was determined using MTT. With the data obtained it was found that the amphotericin B shows no corneal irritation in any of the times evaluated with the evaluation system used. The histological study of tissues exposed to 3% amphotericin B ointment and placebo or PBS revealed that after exposure during 10 minutes or 2 and 24 hours tissues remained essentially normal.

In conclusion, the topical formulation 3% amphotericin B ointment but also the placebo are non irritant for skin and eyes, with a % of cell viability>95% and no histological damages.

In Vitro Skin Corrosion Test (Adapted from OECD Guideline No. 431):

To evaluate skin corrosion a reconstructed human tissue model (RHE) in three dimensions was used. With the data obtained it was found that amphotericin B does not show skin corrosion with the evaluation system.

The histological study of tissues exposed to 3% amphotericin B ointment and placebo or PBS revealed that after exposure during 1 hour tissues remained histologically normal. In conclusion, the cream product formulation is not corrosive for human skin.

Phototoxicity/Photosensitisation Potential: The OECD Guideline No 432 was Followed.

The in vitro 3T3 NRU phototoxicity test was used to identify the phototoxic potential of 3% cream product formulation induced by the excited chemical after exposure to light. In our results, 3% amphotericin b ointment and placebo showed a PIF<1 suggesting that these compounds are not phototoxic whereas doxycycline (positive control) showed a PIF value of 9.3 and therefore, is considered phototoxic. In conclusion, the cream product formulation is not phototoxic.

Acute Dermal Toxicity: This Study Followed the OECD Test Guideline 402.

For the study females rats (Wistar), healthy, with intact skin were used. 13 animals were used, divided into three groups, which were applied the product under study, amphotericin B to 3% (5 animals), placebo (5 animals) or were left untreated (3 animals). The observation period was for 14 days. In general, there was no clinical evidence of signs of toxicity or toxic effects.

In conclusion, under the test conditions, the product 3% amphotericin B ointment was not toxic to the skin after topical application at one dose in rats.

Our results demonstrate substantial differences in the availability of the amphotericin B in urine and serum when is administered topically. After a single application of 40 mg of 3% amphotericin B ointment not any concentration of amphotericin B was found in serum 14 days after exposure, suggesting a faster elimination rate. On the other hands, in urine amphotericin B was detected at a concentration of 0.306 ug/ml. The presence of amphotericin B in urine after 14 days is in agreement with the half life of elimination of 15 days reported previously, probably due to the high binding of amphotericin B to peripheral tissues.

ADME Studies (Toxicokinetic): In this Study of Toxicokinetics the OECD Guideline No. 417 was Followed.

This study is designed to know absorption, distribution, excretion, and metabolism of topical preparation of 3% amphotericin B. The results of these studies provide the basis for the classification of the toxicity of substances, as well as for dose selection in other toxicity studies. The objective was to determine the absorption, distribution, metabolism and excretion of amphotericin B administered topically, using the rat as an experimental model. As a test substance, it was used an ointment preparation containing 3% amphotericin B. Only females Wistar rats were used (n=6).

RESULTS

After a single application of 40 mg of 3% amphotericin B ointment, amphotericin B was detected in urine at 6 and 72 hours after exposure a very low concentration (0.0023 µg/ml and 0.0098 µg/ml, respectively. Presence of amphotericin B in urine after 72 hours may be due to the biphasic elimination described for amphotericin B, in which the half life (t) in the initial phase is 24 hours to 48 hours, followed by a last elimination phase with a longer half life of 15 days, probably due to the high binding of amphotericin B to peripheral tissues.

It is known that pharmacokinetic of amphotericin B is relatively complex and follows a bi- or tri-compartmental model. Although most of the studies have been done using the liposomal or deoxycholate amphotericin B, the distribution and elimination phases vary depending of the formulation and route of administration due to the physicochemical characteristics of this molecule, the adopted configurational structure, the size and the lipid composition.

Preclinical Efficacy Summary:

The cream formulation of the present invention, is effective in treatment of cutaneous leishmaniasis in the experimental animal model with cure rates comparable to those seen when meglumina antimoniate is used.

Preclinical Toxicokinetic Summary:

The cream formulation—Amphotericine B 3% in topical formulation is absorbed thought the skin. Is also distributed to tissue, metabolized by liver and excreted by kidney.

Preclinical Toxicology Summary

3% amphotericin B ointment clearly is not toxic to animals.

Clinical Response of Cream Product Formulation in Patients with Cutaneous Leishmaniasis: Case Report.

The efficacy of amphotericin B 3% was evaluated in patients with diagnosis of cutaneous leshmaniasis by *L. panamensis*. Patients were treated with the ointment 3 times/day/15-28 days. Patients are being followed with clinical evaluation during the treatment, at the end of the treatment and thereafter at 1.5 months, 3 months, 6 months and 12 months. Currently, all the patients showed complete clinical cure at 6 weeks after the end of treatment.

Although the present invention has been described herein with reference to the foregoing exemplary embodiment, this embodiment does not serve to limit the scope of the present invention. Accordingly, those skilled in the art to which the present invention pertains will appreciate that various modifications are possible, without departing from the technical spirit of the present invention.

We claim:

1. A cream formulation for topical application to a patient's mucous tissue and/or skin against diseases produced by leishmaniasis, said formulation consisting of:
    Amphotericin B as a pharmaceutical active ingredient from 0.3% to 3.0% by weight;
    sodium methylparaben in 0.10% by weight;
    sodium propylparaben in 0.02% by weight;
    monobasic sodium phosphate in 0.96% by weight;
    cetyl alcohol in 5.0% by weight;
    light mineral oil in 4.0% by weight;
    mixture of: Cetyl alcohol, Glyceryl Stearate, PEG-75 Stearate, Ceteth-20 and Steareth-20 in 2.90% by weight;
    white petrolatum in 10.0% by weight;
    glycerol monostearate in 0.7% by weight; and
    water from 76.02% to 73.32% by weight.

2. The cream formulation according to claim 1, wherein said cream formulation is applied for 15 days.

3. The cream formulation according to claim 1, wherein said cream formulation has a 62.5% healing rate.

4. The cream formulation according to claim 1, wherein said cream formulation has a 75% healing rate.

5. The cream formulation of claim 1, wherein said formulation is administered topically to at least one of: mucous tissue and skin.

6. The cream formulation according to claim 1, wherein said cream formulation is topically administered to a patient's mucous tissue or skin once a day.

7. The cream formulation according to claim 1, wherein said cream formulation is topically administered to a patient's mucous tissue or skin twice a day.

8. The cream formulation according to claim 1, wherein said cream formulation is applied for 15 days.

* * * * *